US012397030B2

(12) United States Patent
O'Connor et al.

(10) Patent No.: US 12,397,030 B2
(45) Date of Patent: Aug. 26, 2025

(54) POLYPHENOL COMPOSITIONS AND USES THEREOF

(71) Applicant: METAGENICS, INC., Aliso Viejo, CA (US)

(72) Inventors: Annalouise O'Connor, Gig Harbor, WA (US); Mark Houston, Nashville, TN (US)

(73) Assignee: METAGENICS LLC, Aliso Viejo, CA (US)

( * ) Notice: Subject to any disclaimer, the term of this patent is extended or adjusted under 35 U.S.C. 154(b) by 472 days.

(21) Appl. No.: 17/784,168

(22) PCT Filed: Dec. 23, 2020

(86) PCT No.: PCT/US2020/066905
§ 371 (c)(1),
(2) Date: Jun. 10, 2022

(87) PCT Pub. No.: WO2021/133950
PCT Pub. Date: Jul. 1, 2021

(65) Prior Publication Data
US 2023/0030835 A1 Feb. 2, 2023

Related U.S. Application Data

(60) Provisional application No. 62/952,745, filed on Dec. 23, 2019.

(51) Int. Cl.
| | |
|---|---|
| *A61K 36/185* | (2006.01) |
| *A61K 31/01* | (2006.01) |
| *A61K 31/05* | (2006.01) |
| *A61K 31/352* | (2006.01) |
| *A61P 3/06* | (2006.01) |

(52) U.S. Cl.
CPC ............ *A61K 36/185* (2013.01); *A61K 31/01* (2013.01); *A61K 31/05* (2013.01); *A61K 31/352* (2013.01); *A61P 3/06* (2018.01)

(58) Field of Classification Search
None
See application file for complete search history.

(56) References Cited

U.S. PATENT DOCUMENTS

| | | | |
|---|---|---|---|
| 7,638,640 B2 | 12/2009 | Seeram et al. | |
| 7,897,791 B2 | 3/2011 | Seeram et al. | |
| 7,919,636 B2 | 4/2011 | Seeram et al. | |
| 8,648,112 B2 | 2/2014 | Seeram et al. | |
| 10,537,516 B2 | 1/2020 | Zhang et al. | |
| 2004/0131656 A1* | 7/2004 | Roufs | A61K 36/53 514/456 |
| 2008/0248129 A1 | 10/2008 | Bartunek et al. | |
| 2019/0224193 A1 | 7/2019 | Reid et al. | |
| 2020/0085895 A1 | 3/2020 | Patel et al. | |
| 2021/0369674 A1 | 12/2021 | Wan | |

FOREIGN PATENT DOCUMENTS

| | | |
|---|---|---|
| WO | 2005107729 A1 | 11/2005 |
| WO | 2012088519 A2 | 6/2012 |

OTHER PUBLICATIONS

Zhang et al., Aquaculture, 578, 2024, pp. 1-7.*
Pisipati et al., Journal of basic clinical pharmacy, May 2012, pp. 261-264.*
UCLA health, 2022, pp. 1-6.*
Adams LS, et al. Adams, Lynn S., et al. "Pomegranate ellagitannin-derived compounds exhibit antiproliferative and antiaromatase activity in breast cancer cells in vitro." Cancer Prevention Research 3.1, 108-113 (2010).
Cahill LE, et al. Cholesterol efflux capacity, HDL cholesterol, and risk of coronary heart disease: a nested case-control study in men. J Lipid Res., 60(8) 1457-1464 (2019).
Cho, et al. "Chemopreventive activity of ellagitannins and their derivatives from black raspberry seeds on HT-29 colon cancer cells." Food & function 6.5, 1675-1683 (2015).
Cortes-Martin A, et al., "The gut microbiota urolithin metabotypes revisited: the human metabolism of ellagic acid is mainly determined by aging." Food & function 9.8, 4100-4106 (2018).
Cortes-Martin A, et al., "Urolithin metabotypes can anticipate the different restoration of the gut microbiota and anthropometric profiles during the first year postpartum." Nutrients 11.9: 2079 (2019).
Daniel EM, et al., "The effects of pH and rat intestinal contents on the liberation of ellagic acid from purified and crude ellagitannins." Journal of Natural Products 54.4, 946-952 (1991).
Zhao W, et al. "Preparative isolation and purification of urolithins from the intestinal metabolites of pomegranate ellagitannins by high-speed counter-current chromatography." J Chromatogr B Analyt Technol Biomed Life Sci. 990:111-117 (2015).
Derosa G, et al. "Ellagic Acid and Its Role in Chronic Diseases", Advances in Experimental Medicine and Biology, Anti-inflammatory Nutraceuticals and Chronic Diseases vol. 928, 473-479 (2016).

(Continued)

*Primary Examiner* — Michael V Meller
(74) *Attorney, Agent, or Firm* — WARNER NORCROSS + JUDD LLP

(57) ABSTRACT

This disclosure provides a composition and a method for enhancing urolithin B production. As a result of this, due to known impact of urolithin B, this can enhance reverse cholesterol transport and HDL function and management of plasma lipid profile through enhanced production of urolithin B from pomegranate polyphenols by administering a composition comprising a synergistic mixture of pomegranate polyphenols, lycopene and quercetin. The improved HDL function and lipid profile of such composition may be attributed to the enhanced urolithin B production made possible by the combination. Increasing the levels of urolithin B through modulation of the intestinal microbiome metabolism of pomegranate polyphenols is a potential therapeutic target for managing these diseases.

4 Claims, No Drawings

(56) References Cited

OTHER PUBLICATIONS

Ebtehaj S, et al. "HDL (high-density lipoprotein) cholesterol efflux capacity is associated with incident cardiovascular disease in the general population: a case-control study from the PREVEND cohort." Arterioscler Thromb Vasc Biol., 39(9):1874-1883 (2019).
Etxeberria U, et al. "Reshaping faecal gut microbiota composition by the intake of trans-resveratrol and quercetin in high-fat sucrose diet-fed rats." The Journal of nutritional biochemistry 26.6, 651-660 (2015).
Fadaei R, et al. "Impaired HDL cholesterol efflux capacity in patients with non-alcoholic fatty liver disease is associated with subclinical atherosclerosis". Scientific Reports, 8(1), 11691— (2018).
Garcia-Villalba R, et al. "Gastrointestinal simulation model TWIN-SHIME shows differences between human urolithin-metabotypes in gut microbiota composition, pomegranate polyphenol metabolism, and transport along the intestinal tract." Journal of agricultural and food chemistry 65.27, 5480-5493 (2017).
Gibson GR, et al. "Expert consensus document: The International Scientific Association for Probiotics and Prebiotics (ISAPP) consensus statement on the definition and scope of prebiotics." Nat Rev Gastroenterol Hepatol. 14(8):491-502.(2017).
Gimenez-Bastida JA, et al. "Urolithins, ellagitannin metabolites produced by colon microbiota, inhibit quorum sensing in Yersinia enterocolitica: phenotypic response and associated molecular changes. ".Food Chem.132(3):1465-1474 (2012).
Gonzalez-Sarrias A, et al. "Clustering according to urolithin metabotype explains the interindividual variability in the Improvement of cardiovascular risk biomarkers in overweight?obese individuals consuming pomegranate: a randomized clinical trial." Mol Nutr Food Res.61(5). (2017).
Guerin M, et al. Association of Serum Cholesterol Efflux Capacity With Mortality in Patients With ST-Segment Elevation Myocardial Infarction. Journal of the American College of Cardiology, J Am Coll Cardiol. 72(25):3259-3269 (2018).
Kajani S, et al. "Unravelling HDL—Looking beyond the Cholesterol Surface to the Quality Within." Int J Mol Sci, 19(7) (2018).
Kawabata K, et al. "Role of Intestinal Microbiota in the Bioavailability and Physiological Functions of Dietary Polyphenols". Molecules, 24(2) (2019).
Khera AV, et al. "Cholesterol Efflux Capacity, High-Density Lipoprotein Function, and Atherosclerosis." N Engl J Med. 364(2):127-135 (2011).
Lee G, et al. "Anti-inflammatory and antioxidant mechanisms of urolithin B in activated microglia." Phytomedicine, 55:50-57 (2019).
Lei F, et al. J Chromatogr B Analyt Technol Biomed Life Sci. 2003;796(1):189-194. "Pharmacokinetic study of ellagic acid in rat after oral administration of pomegranate leaf extract." J Chromatogr B Analyt Technol Biomed Life Sci. 2003;796(1):189-194.
Li CC, et al. "Tomato Powder Inhibits Hepatic Steatosis and Inflammation Potentially Through Restoring SIRT1 Activity and Adiponectin Function Independent of Carotenoid Cleavage Enzymes in Mice." Mol Nutr Food Res., 62(8):e1700738 (2018).
Nie J, et al. "Quercetin reduces atherosclerotic lesions by altering the gut microbiota and reducing atherogenic lipid metabolites." J Appl Microbiol. 127(6):1824-1834 (2019).
Piwowarski JP, et al. "Urolithins, gut microbiota-derived metabolites of ellagitannins, inhibit LPS-induced inflammation in RAW 264.7 murine macrophages." Mol Nutr Food Res.59(11):2168-2177 (2015).
Porras D, et al. "Protective effect of quercetin on high-fat diet-induced non-alcoholic fatty liver disease in mice is mediated by modulating intestinal microbiota imbalance and related gut-liver axis activation." Free Radic Biol Med. 102:188-202 (2017).
Pereira-Caro G, et al. "In vitro colonic catabolismof orange juice (poly) phenols." Mol Nutr Food Res. 59(3):465-475 (2015).
Qiu Z, et al. "In vitro antioxidant and antiproliferative effects of ellagic acid and its colonic metabolite, urolithins, on human bladder cancer T24 cells." Food Chem Toxicol. 59:428-437 (2013).
Rodriguez J, et al. "Urolithin B, a newly identified regulator of skeletal muscle mass." J Cachexia Sarcopenia Muscle. 8(4):583-597 (2017).
Romo-Vaquero M, et al. "Deciphering the Human Gut Microbiome of Urolithin Metabotypes: Association with Enterotypes and Potential Cardiometabolic Health Implications." Mol Nutr Food Res. 63(4):e1800958 (2019).
Savi M, et al. "In vivo administration of urolithin A and B prevents the occurrence of cardiac dysfunction in streptozotocin-induced diabetic rats." Cardiovasc Diabetol. 16(1):80 (2017).
Seeram NP, et al. "Bioavailability of ellagic acid in human plasma after consumption of ellagitannins from pomegranate (*Punica granatum* L.) juice." Clin Chim Acta. 348(1-2):63-68 (2004).
Seeram NP, et al. "Pomegranate Juice Ellagitannin Metabolites Are Present in Human Plasma and Some Persist in Urine for Up to 48 Hours." J Nutr. 136(10):2481-2485 (2006).
Speer T, et al. "Abnormal High-Density Lipoprotein Induces Endothelial Dysfunction via Activation of Toll-like Receptor-2." Immunity. 38(4):754-768 (2013).
Tamura M, et al. "Quercetin metabolism by fecal microbiota from healthy elderly human subjects." PLoS One. 12(11):e0188271 (2017).
Tomas-Barberan FA, et al. "Ellagic Acid Metabolism by Human Gut Microbiota: Consistent Observation of Three Urolithin Phenotypes in Intervention Trials, Independent of Food Source, Age, and Health Status." J Agric Food Chem.62(28):6535-6538 (2014).
Manach C, et al. "Addressing the inter-individual variation in response to consumption of plant food bioactives: Towards a better understanding of their role in healthy aging and cardiometabolic risk reduction." Mol Nutr Food Res. 61(1) (2017).
Wang S, et al. "Bacteriostatic Effect of Quercetin as an Antibiotic Alternative In Vivo and Its Antibacterial Mechanism In Vitro." Journal of Food Prot. 81(1):68-78 (2018).
Watanabe J, et al. "Proteomic profiling following immunoaffinity capture of high-density lipoprotein: Association of acute-phase proteins and complement factors with proinflammatory high-density lipoprotein in rheumatoid arthritis." Arthritis Rheum. 64(6):1828-1837 (2012).
Wiese M, et al. "Prebiotic Effect of Lycopene and Dark Chocolate on Gut Microbiome with Systemic Changes in Liver Metabolism, Skeletal Muscles and Skin in Moderately Obese Persons." Biomed Res Int. 2019:4625279 (2019).
Wu S, et al., "Diverse Phytochemicals and Bioactivities in the Ancient Fruit and Modern Functional Food Pomegranate (*Punica granatum*)," Molecules. 2017;22(10).
Xia H, et al. "Dietary Tomato Powder Inhibits High-Fat Diet-Promoted Hepatocellular Carcinoma with Alteration of Gut Microbiota in Mice Lacking Carotenoid Cleavage Enzymes." Cancer Prev Res (Phila). 11(12):797-810 (2018).
Yuan T, et al. "Pomegranate's Neuroprotective Effects against Alzheimer's Disease Are Mediated by Urolithins, Its Ellagitannin-Gut Microbial Derived Metabolites." ACS Chem Neurosci. 7(1):26-33 (2016).
Zhao L, et al. "A combination of quercetin and resveratrol reduces obesity in high-fat diet-fed rats by modulation of gut microbiota." Food Funct. 8(12):4644-4656 (2017).
Zhao W, et al. "A Novel Candidate for Prevention and Treatment of Atherosclerosis: Urolithin B Decreases Lipid Plaque Deposition in apoE?/? Mice and Increases Early Stages of Reverse Cholesterol Transport in ox-LDL Treated Macrophages Cells." Mol Nutr Food Res. 63(10):e1800887 (2019).
DaSilva NA, Nahar PP, Ma H, Eid A, Wei Z, Meschwitz S, Zawia NH, Slitt AL, Seeram NP. Pomegranate ellagitannin-gut microbial-derived metabolites, urolithins, inhibit neuroinflammation in vitro. Nutr Neurosci. Mar. 2019,22(3):185-195.
International Search Report for PCT/US2020/066905 dated Apr. 26, 2021, 5 pages.
Eleonora Turrini, Lorenzo Ferruzzi, Carmela Fimognari, "Potential Effects of Pomegranate Polyphenols in Cancer Prevention and Therapy", Oxidative Medicine and Cellular Longevity, vol. 2015, Article ID 938475, 19 pages, 2015.
Shahkoomahally et al., "Profiling phenolic compounds in juice and peel of fourteen pomegranate (*Punica granatum* L.) varieties grown in Florida, USA", Food Chemistry Advances vol. 2, 100225 (2023).

(56) References Cited

OTHER PUBLICATIONS

University Hospitals, Health & Wellness Library Nutrition Facts: Pomegranates, found at: https://www.uhhospitals.org/health-information/health-and-wellness-library/article/nutritionfacts-v1/pomegranates-raw-1-pomegranate-3-38-dia (accessed Mar. 4, 2025).

* cited by examiner

POLYPHENOL COMPOSITIONS AND USES THEREOF

CROSS-REFERENCE TO RELATED APPLICATIONS

This application is the U.S. National Stage of International Application No. PCT/US2020/066905, filed on 23 Dec. 2020, which claims priority to and all advantages of U.S. Provisional Patent Application No. 62/952,745, filed on 23 Dec. 2019, the content of which is incorporated herein by reference.

TECHNICAL FIELD

The present invention generally relates to a composition comprising a synergistic combination of pomegranate polyphenols, quercetin, and lycopene. The composition generally encourages urolithin B production, and is generally useful for treating dyslipidemia, high cholesterol, and the like.

BACKGROUND OF THE INVENTION

Pomegranates are rich in polyphenolic compounds. Of these polyphenols, ellagic acid and ellagitannins, such as punicalagins are found in rich concentrations in the pomegranate fruit peel.[1] Ellagic acid is found free in pomegranate and other fruits, and can also be formed through acid-driven hydrolysis of ellagitannins such as punicalagins, for example in the intestinal tract.[2] Ellagic acid has anti-oxidant properties,[3] however, the absorption of intact ellagic acid in humans is low and is rapidly cleared from plasma.[4,5] In humans, ellagic acid appears within ~30 minutes following consumption, and was not detected by 5-hours with an elimination half-life of 0.71 hours.[6] However, the impact of ellagic acid can be prolonged through its biotransformation in the intestine into metabolically active metabolites known as urolithins[7] Ellagic acid is a precursor to urolithins via hydrolysis, methylation, decarboxylation and dihydroxylation from ellagic acid by the intestinal microbiota.

Specifically, urolithins are metabolites, formed in the intestine through a series of hydrolysis, methylation, decarboxylation and dihydroxylation reactions from ellagic acid by the intestinal microbiota.[8] There are several urolithins, namely urolithin A, urolithin B and isourolithin A.[9] These urolithins are absorbed in the intestine and appear in plasma and are secreted in the urine after 12 hours and for up to 48 hours following consumption of a source of ellagic acid,[6] reflecting the biotransformation in the intestine. People's microbiome produce different urolithins in response to ellagic acid intake, and urolithin "metabotypes" have been described. Namely, in response to ellagic acid intake, individuals can be stratified based on the urolithins detected in urine. Individuals with urolithin metabotypes A (UMA) produce urolithin A after a challenge with high ellagic acid food source.[10] Urolithin metabotype B (UMB) individuals produce urolithin B after a high ellagic acid food source,[10] and urolithin metabotype 0 (UM0) individuals do not produce urolithins in response to ellagic acid challenge.[10] UMB is present in ~10-50% of the individuals tested in a range of clinical trials.[10] Aging has been shown to be a driving factor in the development of UMB.[11] Urolithin metabotype can be assessed through analysis of urolithins and urolithin metabolites present in circulation and in urine.

UMB individuals have been demonstrated to experience a more positive benefit of pomegranate polyphenol supplementation based on plasma lipid profile. This work showed that in middle aged subjects with BMI>27 kg/m² (i.e., overweight or obese individuals), only individuals capable of producing urolithin B (i.e., UMB individuals) experienced a significant reduction in plasma lipid profile (e.g., total cholesterol, LDL, triglycerides, non-HDL-cholesterol, apolipoprotein B, and oxidized LDL).[12] Recently, urolithin B was shown to enhance reverse cholesterol transport, through upregulation of ATP-binding cassette transporter A1 (ABCA1) expression in macrophages.[13] As a regulator of cellular cholesterol, ABCA1 is important in the efflux of cellular cholesterol to the HDL particle, representing the first step of reverse cholesterol transport. HDL function including the ability to efflux cholesterol from cells to HDL significantly predicts the risk of cardiovascular disease and mortality.[14-16] Additionally, in various model systems, urolithin B has been shown to have other benefits including anti-oxidant,[17] anti-inflammatory,[18] neuroprotective,[19-21] cardioprotective,[22] growth and differentiation and myotubes and muscle hypertrophy,[23] anti-proliferative/chemopreventive effects in cancer cell model systems,[24-26] and reduction of quorum sensing in pathogenic bacteria.[27]

Given that urolithins are produced through the actions of the intestinal microbiome, understanding the differences in the intestinal microbiome members and their abundance is of interest. Ellagic acid intervention studies in healthy cohorts including participants who are normal weight as well as overweight have identified differences in intestinal microbial community structure.[28,29]

"Prebiotics" are substrates that are selectively utilized by the microbiota that confer a health benefit. Polyphenols are prebiotics[30] and influence the growth of specific microbiota and thus alter the microbiome of the intestine upon ingestion. For example, lycopene, a polyphenol found in tomatoes, has been shown to modulate the intestinal microbiome in humans[31] and rodent models.[32,33] Additionally, quercetin was shown to have prebiotic effects in both humans,[34] rodents,[35-38] and chickens.[39]

With the pronounced impact of pomegranate supplementation on dyslipidemia in UMB individuals, there is an opportunity to develop a composition having combinations of ingredients that interact to provide this therapeutic impact for individuals with dyslipidemia, regardless of their metabotype. This opportunity is accentuated by the cumbersome, specialized analytical techniques that are generally commercially unavailable to assess urolithin metabotype. Further, there is an opportunity to provide a method to shift the intestinal microbial metabolism towards urolithin B production.

PRIOR ART DOCUMENTS

Non-Patent Literature (NPL) Documents (Generally Referenced Herein Via Superscripts)

1. Wu S, et al. *Molecules.* 2017; 22(10).
2. Daniel E M, et al. *J Nat Prod.* 1991; 54(4):946-952.
3. Derosa G, et al. *Adv Exp Med Biol.* 2016; 928:473-479.
4. Lei F, et al. *J Chromatogr B Analyt Technol Biomed Life Sci.* 2003; 796(1):189-194.
5. Seeram N P, et al. *Clin Chim Acta.* 2004; 348(1-2):63-68.
6. Seeram N P, et al. *J Nutr.* 2006; 136(10):2481-2485.
7. Tomas-Barberan F A, et al. *Mol Nutr Food Res.* 2017; 61(1).
8. Kawabata K, et al. *Molecules.* 2019; 24(2).
9. Garcia-Villalba R, et al. *J Agric Food Chem.* 2017; 65(27):5480-5493.

10. Tomas-Barberan F A, et al. *J Agric Food Chem.* 2014; 62(28):6535-6538.
11. Cortes-Martin A, et al. *Food Funct.* 2018; 9(8):4100-4106.
12. Gonzalez-Sarrias A, et al. *Mol Nutr Food Res.* 2017; 61(5).
13. Zhao W, et al. *Mol Nutr Food Res.* 2019; 63(10): e1800887.
14. Ebtehaj S, et al. *Arterioscler Thromb Vasc Biol.* 2019; 39(9):1874-1883.
15. Cahill L E, et al. *J Lipid Res.* 2019; 60(8):1457-1464.
16. Guerin M, et al. *J Am Coll Cardiol.* 2018; 72(25):3259-3269.
17. Zhao W, et al. *J Chromatogr B Analyt Technol Biomed Life Sci.* 2015; 990:111-117.
18. Piwowarski J P, et al. *Mol Nutr Food Res.* 2015; 59(11):2168-2177.
19. DaSilva N A, et al. *Nutr Neurosci.* 2019; 22(3):185-195.
20. Lee G, et al. *Phytomedicine.* 2019; 55:50-57.
21. Yuan T, et al. *ACS Chem Neurosci.* 2016; 7(1):26-33.
22. Savi M, et al. *Cardiovasc Diabetol.* 2017; 16(1):80.
23. Rodriguez J, et al. *J Cachexia Sarcopenia Muscle.* 2017; 8(4):583-597.
24. Cho H, et al. *Food Funct.* 2015; 6(5):1675-1683.
25. Adams L S, et al. *Cancer Prev Res* (Phila). 2010; 3(1):108-113.
26. Qiu Z, et al. *Food Chem Toxicol.* 2013; 59:428-437.
27. Gimenez-Bastida J A, et al. *Food Chem.* 2012; 132(3): 1465-1474.
28. Romo-Vaquero M, et al. *Mol Nutr Food Res.* 2019; 63(4):e1800958.
29. Cortes-Martin A, et al. *Nutrients.* 2019; 11(9).
30. Gibson G R, et al. *Nat Rev Gastroenterol Hepatol.* 2017; 14(8):491-502.
31. Wiese M, et al. *Biomed Res Int.* 2019; 2019:4625279.
32. Xia H, et al. *Cancer Prev Res* (Phila). 2018; 11(12): 797-810.
33. Li C C, et al. *Mol Nutr Food Res.* 2018; 62(8):e1700738.
34. Tamura M, et al. *PLoS One.* 2017; 12(11):e0188271.
35. Porras D, et al. *Free Radic Biol Med.* 2017; 102:188-202.
36. Nie J, et al. *J Appl Microbiol.* 2019; 127(6):1824-1834.
37. Etxeberria U, et al. *J Nutr Biochem.* 2015; 26(6):651-660.
38. Zhao L, et al. *Food Funct.* 2017; 8(12):4644-4656.
39. Wang S, et al. *J Food Prot.* 2018; 81(1):68-78.
40. Kajani S, et al. *Intl Mol Sci.* 2018; 19(7).
41. Khera A V, et al. *N Engl J Med.* 2011; 364(2):127-135.
42. Speer T, et al. *Immunity.* 2013; 38(4):754-768.
43. Watanabe J, et al. *Arthritis Rheum.* 2012; 64(6):1828-1837.
44. Fadaei R, et al. *Sci Rep.* 2018; 8(1):11691.
45. Pereira-Caro G, et al. *Mol Nutr Food Res.* 2015; 59(3): 465-475.

SUMMARY OF THE INVENTION

Provided herein is a composition for administration to a subject. Also provided herein are methods and uses associated with the composition. The composition generally comprises pomegranate extract (e.g. pomegranate polyphenols), quercetin, and lycopene. It has been surprisingly found that the combination of pomegranate polyphenols, quercetin, and lycopene is synergistic as a therapeutic strategy to shift the intestinal microbial metabolism towards urolithin B production. In addition, the present disclosure provides proof-of-principle that synergistic actions of the composition on urolithin B production represent a desirable strategy for high-density lipoprotein (HDL) function and dyslipidemia management.

DETAILED DESCRIPTION OF THE INVENTION

The composition of this disclosure comprises pomegranate, quercetin, and lycopene. In various embodiments, the pomegranate is further defined as a pomegranate extract. As understood in the art, pomegranate, and thus pomegranate extract, comprises polyphenols. As such, the composition generally comprises pomegranate polyphenols, quercetin, and lycopene. The pomegranate polyphenols, quercetin, and lycopene are generally considered to be "actives" of the composition.

In certain embodiments, the composition consists essentially of, or consists of, the pomegranate polyphenols, quercetin, and lycopene as actives of the composition. In specific embodiments, the composition is generally free of other components that would be construed as being "actives," although the composition can include one or more conventional "inactives" as understood in the art.

As used herein, the phrase "consisting essentially of" generally encompasses the specifically recited elements/components for a particular embodiment. Further, the phrase "consisting essentially of" generally encompasses and allows for the presence of additional or optional elements/components that do not materially impact the basic and/or novel characteristics of that particular embodiment. In certain embodiments, "consisting essentially of" allows for the presence of $\leq 10$, $\leq 5$, or $\leq 1$, weight percent (wt. %) of additional or optional components based on the total weight of the composition.

Components that would generally materially impact the composition of this disclosure include active ingredients that are different from pomegranate polyphenols, quercetin, and lycopene. In certain embodiments, the composition of this disclosure is substantially free of or free of other active ingredients.

In various embodiments, the composition of this disclosure optionally may contain a number of other actives; however, it must contain a whole-fruit pomegranate (Punica granatum) extract enriched in total polyphenols and specifically ellagitannins, quercetin, and lycopene and the amounts used may vary up to 50% from the amounts described in the working example below. Such extracts can be produced from whole pomegranate fruit through methods including solvent (alcohol) extraction, or through solvent-free pressed extraction, and followed by a series of filtration and concentration steps to create a polyphenol-rich extract suitable for commercial manufacturing use.

Pomegranate is a fruit-bearing deciduous shrub and the predominant member of two species comprising the Punicaceae family Among seed, peel, and juice, the peel is generally the constituent which possesses higher content of polyphenols. This part of the fruit contains ellagitannins Specifically, pomegranate peel generally contains a high amount of polyphenols, condensed tannins, catechins, and prodelphinidins. In general, the pomegranate extract of the composition is obtained from ripened pomegranate fruit.

Punicalagin, a large polyphenol with a molecular weight greater than 1000, is unique to pomegranate and is part of a family of ellagitannins that includes the minor tannins punicalin and gallagic acid. Pomegranate also contains other polyphenols, such as anthocyanins (3-glucosides and 3,5-glucosides of delphinidin, cyanidin, and pelargonidin) and flavonols. During juice processing, for example, the whole fruit is pressed and ellagitannins are released into pomegranate juice in significant levels (e.g. over 2 g/L juice). This disclosure is not limited to a particular source of the pomegranate extract. Pomegranate extract is commercially available from a number of suppliers.

In various embodiments, the pomegranate extract, e.g. pomegranate polyphenols, is present in the composition in an amount of from about 15 to about 40, optionally of from about 20 to about 35, optionally of from about 25 to about 32.5, optionally of from about 27.5 to about 30, or optionally about 28, wt. %, each based on 100 parts by weight of the combination of the pomegranate extract, quercetin, and lycopene. In certain embodiments, the pomegranate extract, e.g. pomegranate polyphenols, is present in the composition in an amount of from about 200 to about 600, optionally of from about 300 to about 500, optionally of from about 350 to about 450, or optionally about 400, mg, per serving of the composition.

Quercetin is a plant flavonol from the flavonoid group of polyphenols. It is found in many fruits, vegetables, leaves, seeds, and grains; red onions and kale are common foods containing appreciable amounts of quercetin. This disclosure is not limited to a particular source of the quercetin. Quercetin is commercially available from a number of suppliers.

In various embodiments, the quercetin is present in the composition in an amount of from about 35 to about 85, optionally of from about 45 to about 80, optionally of from about 55 to about 75, optionally about 65 to about 72.5, or optionally about 70, wt. %, each based on 100 parts by weight of the combination of the pomegranate extract, quercetin, and lycopene. In certain embodiments, the quercetin is present in the composition in an amount of from about 500 to about 1500, optionally of from about 750 to about 1250, optionally of from about 900 to about 1100, or optionally about 1000, mg, per serving of the composition.

Lycopene is a bright red carotenoid hydrocarbon found in tomatoes and other red fruits and vegetables, such as red carrots, watermelons, grapefruits, and papayas. Lycopene is a symmetrical tetraterpene assembled from eight isoprene units. It is a member of the carotenoid family of compounds, and because it consists entirely of carbon and hydrogen, is also a carotene. Fruits and vegetables that are high in lycopene include autumn olive, gac, tomatoes, watermelon, pink grapefruit, pink guava, papaya, seabuckthorn, wolfberry (goji, a berry relative of tomato), and rosehip. This disclosure is not limited to a particular source of the lycopene. Lycopene is commercially available from a number of suppliers.

In various embodiments, the lycopene is present in the composition in an amount of from about 0.1 to about 5, optionally of from about 0.5 to about 3, optionally of from about 1 to about 2, optionally about 1.25 to 1.75, or optionally about 1.4, wt. %, each based on 100 parts by weight of the combination of the pomegranate extract, quercetin, and lycopene. In certain embodiments, the lycopene is present in the composition in an amount of from about 1 to about 50, optionally of from about 5 to about 40, optionally of from about 10 to about 30, or optionally about 20, mg, per serving of the composition.

The study that resulted in the composition of this disclosure was designed to examine the effect of a combination formulation on the production of urolithin B by fecal microbial communities for the management of plasma lipid profile and reverse cholesterol transport, a key feature of HDL function. Methods and uses of the composition of this disclosure were also discovered.

As used herein, "an effective amount" refers to an amount sufficient for the treatment of diseases at a reasonable benefit/risk ratio applicable to a particular treatment, e.g., medical treatment, and the level of the effective dose may be determined from factors including severity of illness, drug activity, age, genetic background, body weight, health conditions, drug sensitivity of a subject, administration time, administration route and dissolution rate, length of treatment of the formulation of the present disclosure, drug(s) used in combination with or simultaneously with the formulation of the present disclosure, and other factors well known in the medical field. The formulation of the present disclosure may be administered in an effective amount. The formulation of the present disclosure may be administered as an individual therapeutic agent or in combination with other therapeutic agent(s), and also sequentially or simultaneously with the conventional therapeutic agent(s). The formulation of the present disclosure may be administered as a single dose or in multiple divided doses. Additionally, it is important that the least amount which can achieve the maximum effect without any side effects be administered in consideration of all the factors described above. As used and described herein, the dose of the formulation of the present disclosure may be determined by a skilled person in the art considering the intended use(s), severity of disease(s), age, body weight, sex and medical history of a subject, or the kinds of ingredients used as active ingredient(s), etc.

For example, the formulation of the present disclosure may be administered in the range of from about 0.75 mg/kg/day to about 50 mg/kg/day for mammals including humans, or optionally in an amount of from about 8.875 mg/kg/day to about 26.625 mg/kg/day. Where required, the formulation may be administered in amounts as high as 60 mg/kg/day at the discretion of a skilled practitioner. The formulation of the present disclosure may be administered once daily or in a few divided doses, although administration is not particularly limited thereto. However, as described herein the method of the disclosure may require a clinician to consider the specific parameters described herein to assure the dosage is suitable as intended.

As described herein, the pomegranate extract, quercetin, and lycopene referred to are materials that are commercially available. Typically, such commercial products used in formulations comprising a whole fruit pomegranate (Punica granatum) extract with a total polyphenol content (as gallic acid equivalent) of 50% or greater, and a punicalagin content of 30% or greater.

Suitable pomegranate extracts are commercially available from Verdure Sciences of Noblesville, IN, such as those under the trade name POMELLA®. In certain embodiments, suitable pomegranate extract/polyphenols for the composition of this disclosure are as described in U.S. Pat. No. 7,638,640 B2, and/or U.S. Pat. No. 7,897,791 B2, and/or U.S. Pat. No. 7,919,636 B2, each to Seeram et al., and/or as described in US Pub. 2020/0085895 A1 to Patel et al. Suitable extraction techniques are also described in one or more of these references, as well as in U.S. Pat. No. 10,537,516 B2 to Zhang et al., the disclosures of which are incorporated herein by reference in their entirety.

Commercial products used in formulations comprising quercetin typically have a purity of greater than 90%. Commercial products used in formulations comprising lycopene typically have a purity of greater than 10%. Because of the chemical nature of pomegranate, quercetin, and lycopene, solvents may be used in the purification thereof, however, it is preferred that any such solvent be non-toxic, and it is preferred that such solvents be removed before final formulation into a product for human consumption.

In various embodiments, the composition includes one or more additives that are generally used for conventional compositions, including those adapted for oral administration. In certain embodiments, the composition of this disclosure can comprise inactive ingredients as described below. If utilized, the inactive ingredients are different from pomegranate polyphenols, quercetin, and lycopene, and other active ingredients (if present or utilized).

Components that would not generally impact the composition of this disclosure include inactive ingredients. Inactive ingredients are understood in the art and are different from active ingredients, such as those described above. Examples of inactive ingredients include, but are not limited to, vitamins; flavorings; carob; corn syrups, such as hydrolyzed corn syrup solids; cellulose, such as methyl cellulose, hydroxypropyl methyl cellulose, carboxy methyl cellulose, microcrystalline cellulose, and powdered cellulose; fructose; maltodextrin and maltol, such as natural maltol; sorbitol; preservatives; alcohols, such as ethanol, propyl alcohol and benzyl alcohol; glycerin; potassium sorbate; sodium benzoate; binders; flow agents; stearates, such as calcium stearate, magnesium stearate, and sodium magnesium stearate; dicalcium phosphate; glyceryl triacetate; vegetable oils, such as hydrogenated vegetable oils; mineral oils; water; silicones, such as silicone oils; silicon dioxide; stearic acid; waxes, such as carnauba wax and beeswax; starches, such as corn starch and potato starch; fatty esters and fatty alcohols; glycols and polyglycols; and combinations thereof. If utilized to form the composition, the inactive ingredient(s) can be used in various amounts. Further, it is to be appreciated that the amounts of actives described herein can be normalized with respect to 100 parts by weight of the composition to account for the presence of inactive ingredients (if utilized). This disclosure is not limited to a particular inactive ingredient or amount thereof.

The composition can be prepared using various methods understood in the art. For example, actives of the composition, and optionally one or more inactives, can be mixed or blended and compressed or compounded utilizing various techniques understood in the art. The composition of this disclosure is not limited to a particular order of manufacturing steps or method of manufacture.

Typically, the composition is administered (or ingested) orally, e.g. via the mouth (or "per os"). More typically, at least a portion of the composition is administered (or digested) enternally, e.g. via the gastrointestinal (GI) track (or "enteros"). The subject is typically a human, and can include men and women of various ages. The composition of this disclosure is not limited to a particular subject.

The composition can be in various forms. Examples of suitable forms include solids, gels and liquids. Typically, the composition is solid. For example, the composition can be in the form of a pill, including tablets, capsules, and caplets. In general, each of these terms can be used interchangeable in the art, e.g. tablet for pill or vice versa. Other than the pomegranate polyphenols, quercetin, and lycopene (i.e., the "actives" or "active ingredients"), the composition can include inactives (or "inactive ingredients") including, but not limited to, excipients, such as diluents and binders; granulating agents; glidants (or flow aids); fillers; lubricants; preservatives; stabilizers; coatings; disintegrants; sweeteners or flavors; and pigments. Further examples of inactive ingredients are described above. In general, a number and quantity of excipients should be kept at a minimum as long as active ingredients are properly delivered. This is because subjects/consumers tend to prefer smaller tablets for easier consumption.

The composition can be in powder form, or pressed or compacted from a powder into a solid dose. A coating, e.g. polymer coating, may be used to make the tablet smoother and easier to swallow, to control release rate of the actives, to increase resiliency (or shelf life), and/or to enhance appearance. Other suitable oral forms of the composition include syrups, elixirs, suspensions, emulsions, and powders (e.g. for use in making foods, drinks, etc.). Further non-limiting embodiments of the composition of this disclosure are described hereafter.

In various embodiments, each of the pomegranate extract, quercetin, and lycopene is individually available commercially in powder form. Such pomegranate extract, quercetin, and lycopene is useful in the invention due to its ease of handling. Due to the nature of these ingredients and the need for manufacturability, various excipients can be utilized to enable flow, e.g. as listed in Example 1 further below.

As noted above, this formulation may be used as a powder, tablet or capsule. However, in certain embodiments, for ease of handling, the formulation is encapsulated into a capsule.

Dosages or formulations thereof are prepared using methods understood in the art. Similarly, the use of capsules used in preparing a dosage for use by consumers and the like is understood in the art, and methods for making the same are apparent to and understood by those skilled in the art.

In various embodiments, the dose of the product ranges between effective amounts for a majority of individuals/subjects. For total pomegranate polyphenols, this range is about 3 mg to about 1000 mg per day in certain embodiments. For quercetin this range is about 50 mg to about 2000 mg in further or other embodiments. For lycopene this range is about 5 mg to about 1000 mg per day for yet further or other embodiments. Other suitable dosages are described above.

In various embodiments, a synergistic ratio of total weight pomegranate polyphenols ("P") to total weight quercetin and lycopene ("Q+L") in the composition is from about 1:0.1 to about 1:10, optionally in a ratio of from about 1:1 to about 1:5, or optionally in a ratio of about 1:2.5, (P:Q+L).

The composition can be administered in various amounts. The composition may be administered as needed, daily, several times per day or in any suitable regimen such that the desired outcome is achieved. In the method of this disclosure, the frequency of administration (e.g. of ingestion and/or digestion) can depend on several factors, including the desired level of urolithin B production. Generally, a regimen includes administration of the composition once or twice daily to include an administration in the morning and/or an administration in the evening. The amount of composition administered may depend on several factors, including level of desired results and the specific composition.

The follow examples, illustrating the compositions, methods, and uses of this disclosure, are intended to illustrate and not to limit the invention.

EXAMPLES

Example 1—Capsule Composition

An example composition is described and illustrated in Table 1 below. The components/ingredients are available from commercial sources.

The pomegranate polyphenols (or pomegranate extract) is a dry powder commercially available from Verdure Sciences, under the trade name POMELLA®, and product code POM030EPPH. This product is obtained from cultivation and extraction of whole fruit of Punica granatum, and chemical analysis thereof shows an actives content of NLT 30% for punicalagins and NLT 50% for polyphenols.

The components are dry blended to form a mixture, and the mixture is capsuled using conventional techniques understood in the art. The amounts in Table 1 below provides a serving. A typical serving size is four (4) capsules.

TABLE 1

Capsule Composition

| Component/Ingredient | mg (per Serving) |
|---|---|
| Pomegranate polyphenols | 400 |
| Quercetin | 1000 |
| Lycopene | 20 |
| D-Alpha Tocopheryl Succinate (vitamin E) | 268 |
| Microcrystalline cellulose | 144 |
| Silicon dioxide | 27 |
| Magnesium stearate | 27 |

Ingredients and excipients are then sealed within a hard-shell capsule including typical clear vegetable capsules such as hydroxypropyl methylcellulose or hypromellose. Additional excipients may be used to provide necessary bulk and compressibility, and excipients typically are used in an amount of from 0.1 mg to 300 mg. As illustrated above, Example 1 has 198 mg. 268 mg of vitamin E is also present.

Example 2—Tablet Composition

The composition of Example 1 may be compressed into a tablet. The skilled artisan will appreciate that certain excipients are used to provide improved compressibility and release of tablets.

Example 3—Bulk Powder Suitable for an Instant Beverage

The composition of Example 1 may be packaged in bulk, without compressing into a tablet or capsuled, and as such, it can be utilized in a powdered beverage. In this case, a scoop is provided to dispense 7 grams of the composition. In addition to the components in Example 1, flavorings, sweeteners and the like may be dry blended into the formula.

Of course, the skilled artisan will appreciate that a number of excipients are available in the market that can be used to provide improved taste, dissolution and palatability. Such excipients can include: Agglomerated Lactose, Alkali Stearate, Alpha-Lactose Monohydrate, Anhydrous Alpha-Lactose, Anhydrous Beta-Lactose, Calcium Phosphate, Calcium Silicate, Calcium Stearate, Calcium Sulfate, Carboxymethylcellulose Sodium, Cellulose, Copolyvidone, Corn Starch, Corn Syrup, Croscarmellose Sodium, Crospovidone, Dextrates, Dextrose, Dibasic Calcium Phosphate, Dicalcium phosphate, Gelatin, Guar gum, Gum Acacia, Hydrogenated Vegetable oil, Hydroxyethyl Cellulose, Hydroxypropyl Cellulose, Hydroxypropyl Methylcellulose, Lactose Monohydrate, Magnesium Silicate, Magnesium stearate, Maltodextrin, Mannitol, Methylcellulose, Microcrystalline Cellulose, Mineral oil, Modified starch, Native Starch, Pectin, Polydextrose, Polyethylene Glycol, Potato starch, Povidone, Pre-gelatinized Starch, Silica/Silicon Dioxide, Sodium Alginate, Sodium Starch Glycolate, Sodium Stearyl Fumarate, Sorbitol, Starch, Stearic Acid, Sucrose, Sugar, Talc, Tapioca starch, Tragacanth, Tribasic Calcium Phosphate, Tricalcium Phosphate, Wheat starch, and Xylitol—though others may be used.

Examples 4 to 6—Uses of the Composition

It has been previously demonstrated that the production of urolithin B is essential for reducing plasma lipids in response to pomegranate supplementation.[12] Specifically, only individuals capable of producing urolithin B experienced significant reductions in total cholesterol, LDL-cholesterol, non-HDL cholesterol, and plasma triglycerides.[12] These components of the plasma lipid profile significantly increase cardiovascular risk, and management is important for prevention of cardiovascular disease.

Dysfunctional HDL results from metabolic stressors such as pro-oxidant molecules, inflammation or high glucose.[40] Dysfunctional HDL has reduced cholesterol efflux capacity (i.e. ability to efflux cholesterol from cells such as macrophages or atherogenic foam cells) and reduced ability to prevent the oxidation of LDL.[40] Dysfunctional HDL has been correlated with cardiovascular risk.[14-16] Dysfunctional HDL has been identified in several chronic conditions which are characterized by pro-inflammatory, pro-oxidant or hyperglycemic metabolic environment, for example: cardiovascular disease,[41] chronic kidney disease,[42] autoimmune conditions such as rheumatoid arthritis,[43] and other metabolic conditions such as fatty liver disease.[44] Dysfunctional HDL can increase cardiovascular risk in these conditions, further complicating the clinical picture. The composition of this disclosure may appear to promise the restoration or improvement of HDL, specifically as urolithin B has been shown to upregulate components of reverse cholesterol transport, a critical feature of HDL function.[13] Therefore, this example demonstrates the potentiation effect of the composition of this disclosure on improving cardiovascular health in individuals with dyslipidemia or impaired HDL function.

Example 4—Fecal Microbial Production of Urolithin B

Fecal slurry studies treating with single or combined ingredients with the production of urolithin B assessed. Fecal samples from volunteers who had followed a low polyphenol diet for at least 48 hours and had not consumed antibiotics for at least 3 months prior were collected and incubated under aerobic conditions with test compounds (pomegranate extract, quercetin, and lycopene—in the forms described in Detailed Description of the Invention). This methodology has been used previously to assess the microbial metabolism of polyphenols.[45] In these experiments, the addition of quercetin or lycopene alone enhanced the urolithin B production from pomegranate, however the combination of lycopene and quercetin worked synergistically to shift the intestinal microbial metabolism towards the production of urolithin B more than expected from additive effect of either alone:

TABLE 2

Urolithin B production from pomegranate extract in a
human fecal slurry model is enhanced with synergistic
combination of quercetin and lycopene

|  | Urolithin B production |
|---|---|
| Pomegranate extract | + |
| Quercetin | − |
| Lycopene | − |
| Quercetin + Lycopene | − |
| Pomegranate extract + Quercetin | ++ |
| Pomegranate extract + Lycopene | ++ |
| Pomegranate extract + Quercetin + Lycopene | ++++ |

Example 5—Simulated Gut Environment (TWIN-SHIME)

Additionally, studies in a simulated gut environment, such as the Gastrointestinal Simulation Model TWIN-SHIME[9] also indicated that the combination of quercetin and lycopene with pomegranate extract increased Urolithin B production to a greater extent than seen with pomegranate extract alone, quercetin alone, lycopene alone, or the combination of either quercetin or lycopene with pomegranate extract. In these experiments, the addition of quercetin or lycopene alone enhanced the urolithin B production from pomegranate, however the combination of lycopene and quercetin worked synergistically to shift the intestinal microbial metabolism towards the production of urolithin B more than expected from additive effect of either alone:

TABLE 3

Urolithin B production from pomegranate extract in
a simulated gastrointestinal environment is enhanced by
the synergistic combination of quercetin and lycopene

|  | Urolithin B production |
|---|---|
| Pomegranate extract | + |
| Quercetin | − |
| Lycopene | − |
| Quercetin + Lycopene | − |
| Pomegranate extract + Quercetin | ++ |
| Pomegranate extract + Lycopene | ++ |
| Pomegranate extract + Quercetin + Lycopene | ++++ |

Example 6—Enhanced HDL Function and Improvement in Dyslipidemia in Humans

A typical non-urolithin B metabotype subject (100 kg man) with indicators of HDL dysfunction (HDL particle number (HDL-P), myeloperoxidase (MPO), high sensitivity C-Reactive Protein (hsCRP), apolipoprotein A-I (apoA-I) outside normal reference range) and documented dyslipidemia (total cholesterol, LDL-cholesterol, oxidized LDL, HDL-cholesterol, plasma triglycerides outside the normal reference range) consumed the following treatments in random order for 4 weeks each with each phase separated by a 4-week wash-out period: 1) 20 mg lycopene; 2) 1000 mg quercetin; 3) 400 mg pomegranate polyphenols; 4) 20 mg lycopene+1000 mg quercetin; 5) 20 mg lycopene+400 mg pomegranate polyphenols; 6) 1000 mg quercetin+400 mg pomegranate polyphenols; 7) 20 mg lycopene+1000 mg quercetin+400 mg pomegranate polyphenols. For 3-days before and 3-days at the end of each intervention period, the subject was instructed to consume a source of ellagic acid daily, and urolithin metabotype assessed via blood and urine analysis of urolithins and their metabolites. The subject also provided a stool sample to assess intestinal microbial community structure. Additionally, the subject provided a blood sample for assessment of markers of HDL dysfunction and dyslipidemia listed above.

Importantly, compared with the ingredients alone, the combination of lycopene+quercetin+pomegranate polyphenols (Treatment 7) resulted in a greater shift metabolism, favoring the production of urolithin B (Table 4). Interestingly, this combination of lycopene+quercetin+pomegranate (Treatment 7), compared with the ingredients alone, resulted in a greater reduction in plasma total-cholesterol, LDL-cholesterol, oxidized LDL, and plasma triglycerides, and factors associated with HDL dysfunction (MPO and hsCRP). The combination of lycopene+quercetin+pomegranate, compared with the ingredients alone, additional led to greatest improvement in HDL-C and HDL-P concentrations (Table 4):

TABLE 4

Improvement in markers of HDL function, dyslipidemia, and
urolithin B production is enhanced with synergistic combination
of lycopene, quercetin and pomegranate polyphenols

| Treatment | Lycopene (20 mg) | Quercetin (1000 mg) | Pomegranate polyphenols (400 mg) | Improvement in HDL Function Markers | Improvement in Dyslipidemia Markers | Urolithin B production |
|---|---|---|---|---|---|---|
| 1 | + | − | − | + | + | − |
| 2 | − | + | − | + | + | − |
| 3 | − | − | + | + | + | − |
| 4 | + | + | − | ++ | ++ | − |
| 5 | + | − | + | ++ | ++ | + |
| 6 | − | + | + | ++ | ++ | + |
| 7 | + | + | + | ++++ | ++++ | +++ |

Having illustrated the invention and having provided examples of its composition and uses, it is expected that the skilled artisan may not only make and use the invention, but also make and use reasonable variations of the invention within the scope of the following claims.

Additional Embodiments

The following additional embodiments are provided, the numbering of which is not to be construed as designating levels of importance. Moreover, it is to be understood that the embodiments recited below are provided in conjunction with and in addition to the embodiments described above, as well as those claimed further below. Thus, it is also to be understood that variations, combinations, and/or modifications of the embodiment(s) and/or feature(s) of the embodiment(s) may be within the scope of the present invention. Likewise, alternative embodiments that result from combining, integrating, and/or omitting features of the embodiment(s) described herein may also be within the scope of the present invention.

Embodiment 1 relates to a synergistic composition comprising pomegranate extract, quercetin and lycopene.

Embodiment 2 relates to the composition of Embodiment 1, wherein the composition comprises 28.2% by weight pomegranate polyphenols and 71.8% by weight of the combination of quercetin+lycopene.

Embodiment 3 relates to the composition of Embodiment 1, wherein pomegranate with quercetin+lycopene synergistically enhance their therapeutic effect.

Embodiment 4 relates to a method of using the composition of Embodiment 1, comprising ingesting the composition of Embodiment 1 in an amount equivalent to at least 400 mg pomegranate polyphenols and 1000 mg quercetin and 20 mg lycopene.

Embodiment 5 relates to a method of using the composition of Embodiment 1 for the regulation of urolithin B production.

Embodiment 6 relates to a method of using the composition of Embodiment 1 for the regulation of urolithin B production through modulation of the intestinal microbiome.

Embodiment 7 relates to a method of using the composition of Embodiment 1 for the treatment of dyslipidemia, comprising ingesting the composition of Embodiment 1 in an amount sufficient to effect treatment thereof.

Embodiment 8 relates to a method of using the composition of Embodiment 1 for the treatment of HDL function, comprising ingesting the composition of Embodiment 1 in an amount sufficient to effect treatment thereof.

Embodiment 9 relates to a method of using the composition of Embodiment 1 for HDL-P, comprising ingesting the composition of Embodiment 1 in an amount sufficient to provide the desired effect.

Embodiment 10 relates to a method of using the composition of Embodiment 1 for the treatment of HDL cholesterol, comprising ingesting the composition of Embodiment 1 in an amount sufficient to effect treatment thereof.

Embodiment 11 relates to a method of using the composition of Embodiment 1 for the treatment of HDL selected from the group comprising a subspecies or subclass and HDL mapping, comprising ingesting the composition of Embodiment 1 in an amount sufficient to effect treatment thereof.

Embodiment 12 relates to a method of using the composition of Embodiment 1 for the treatment of a urolithin B-related malady that is characterized by a deficiency or reduced production of urolithin B, comprising ingesting the composition of Embodiment 1 in an amount sufficient to effect treatment thereof.

Each of the additional embodiments so defined may be combined with any other embodiment or aspect of the embodiments of the invention described herein. In particular, any feature indicated as being optional or advantageous may be combined with any other feature or features indicated as being optional or advantageous, and each aspect of embodiments of the composition are to be understood as being applicable to use in the embodiments of the methods of using the composition.

The terms "comprising" or "comprise" are used herein in their broadest sense to mean and encompass the notions of "including," "include," "consist(ing) essentially of," and "consist(ing) of." The use of "for example," "e.g.," "such as," and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-25, ±0-10, ±0-5, or ±0-2.5, % of the numerical values. Further, The term "about" applies to both numerical values when associated with a range of values. Moreover, the term "about" may apply to numerical values even when not explicitly stated.

Generally, as used herein a hyphen "-" or dash "—" in a range of values is "to" or "through"; a ">" is "above" or "greater-than"; a "≥" is "at least" or "greater-than or equal to"; a "<" is "below" or "less-than"; and a "≤" is "at most" or "less-than or equal to." On an individual basis, each of the aforementioned applications for patent, patents, and/or patent application publications, is expressly incorporated herein by reference in its entirety in one or more non-limiting embodiments.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

What is claimed is:

1. A composition comprising:
   I) a synergistic combination consisting essentially of:
      i) pomegranate extract with a total polyphenol content of 50% by weight or greater, and a punicalagin content of 30% by weight or greater;
      ii) quercetin; and
      iii) lycopene;
   II) Vitamin E; and
   III) at least one inactive ingredient selected from the group consisting of microcrystalline cellulose, silicon dioxide, magnesium stearate, and combinations thereof;
   wherein the ratio of the total weight of the pomegranate polyphenols to total weight quercetin and lycopene in the composition is from about 1:0.1 to about 1:10;
   wherein the composition is in the form of a serving, and wherein the pomegranate extract is present in the serving in an amount of from about 200 to about 600 mg, the quercetin is present in the serving in an amount of from about 500 to about 1500 mg, and the lycopene is present in the serving in an amount of from about 1 to about 50 mg; and
   wherein the composition is encapsulated in hydroxypropyl methylcellulose or hypromellose and is in the form of at least one tablet, capsule, or caplet.

2. The composition of claim 1, wherein the pomegranate extract is pomegranate polyphenols.

3. The composition of claim 1, wherein the pomegranate extract is present in an amount of from about 15 wt. % to about 40 wt. %, the quercetin is present in an amount of from about 35 wt. % to about 85 wt. %, and the lycopene is present in an amount of from about 0.1 wt. % to about 5 wt. %, each based on 100 parts by weight of the pomegranate extract, quercetin, and lycopene.

4. The composition of claim 1, comprising 28.2% by weight pomegranate polyphenols and 71.8% by weight of the combination of quercetin and lycopene.

* * * * *